United States Patent
Nguyen et al.

(10) Patent No.: US 6,462,214 B1
(45) Date of Patent: Oct. 8, 2002

(54) METHOD OF PREPARING SILACYCLOALKANES

(75) Inventors: Binh Thanh Nguyen, Midland, MI (US); John Patrick Cannady, Midland, MI (US); Yasushi Sugiura, Chiba (JP)

(73) Assignee: Dow Corning Corporation, Midland, MI (US)

( * ) Notice: Subject to any disclaimer, the term of this patent is extended or adjusted under 35 U.S.C. 154(b) by 0 days.

(21) Appl. No.: 10/091,920

(22) Filed: Mar. 5, 2002

(51) Int. Cl.$^7$ ................................................. C07F 7/08
(52) U.S. Cl. ..................................... 556/406; 556/474
(58) Field of Search .................................. 556/406, 474

(56) References Cited

U.S. PATENT DOCUMENTS

| | | | | |
|---|---|---|---|---|
| 4,973,723 A | | 11/1990 | Cawthon et al. ............. | 556/406 |
| 5,015,624 A | * | 5/1991 | Schulz ........................ | 556/474 |
| 5,527,490 A | * | 6/1996 | Kinsho et al. ............... | 556/406 |
| 5,641,431 A | * | 6/1997 | Kinsho et al. ............... | 556/406 |

OTHER PUBLICATIONS

Inst. Petrochem. Syn., Moscow, USSR. Khim. Geterotsikl. Doedin, 1996, "Method of Functional Analysis of Organosilicon Compounds Containing Silacyclobutane Groups". (Abstract Only).

Journal of the American Chemical Society, "Synthesis of Silacyclobutane and Some Related Compounds," J.Laane, 1967, 89(5), pp. 1144–1147.

\* cited by examiner

*Primary Examiner*—Paul F. Shaver
(74) *Attorney, Agent, or Firm*—Larry A. Milco

(57) ABSTRACT

According to the present invention, a method of preparing a silacycloalkane, comprising the steps of (A) adding a substituted silacycloalkane having the formula:

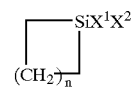

wherein $X^1$ is —F, —Cl, —Br, or —OR$^1$ and $X^2$ is $X^1$ or H, wherein $R^1$ is $C_1$–$C_8$ hydrocarbyl, and n is 1, 2, or 3, to a suspension of lithium aluminum hydride in a glycol diether at a temperature not greater than 50° C. to form a mixture, wherein the glycol diether consists essentially of a linear arrangement of oxyalkylene units having formulae independently selected from —OCH$_2$CH$_2$—, —OCH$_2$CH(CH$_3$)—, and —OCH$_2$CH(CH$_2$CH$_3$)—, and end-groups having the formulae —R$^2$ and —OR$^2$, wherein each R$^2$ is independently selected from $C_1$–$C_8$ alkyl, phenyl, and $C_1$–$C_8$ alkyl-substituted phenyl, provided the glycol diether has a normal boiling point of at least 85° C. and a viscosity not greater than 3000 mm$^2$/s at 25° C.; and (B) distilling the mixture under reduced pressure at a temperature not greater than 50° C. to remove the silacycloalkane.

20 Claims, No Drawings

METHOD OF PREPARING SILACYCLOALKANES

FIELD OF THE INVENTION

The present invention relates to a method of preparing a silacycloalkane and more particularly to a method comprising adding an Si-substituted silacycloalkane to a suspension of lithium aluminum hydride in a glycol diether. The present invention also relates to a method of preparing a silicon carbide film using the silacycloalkane.

BACKGROUND OF THE INVENTION

Methods of preparing silacycloalkanes are known in the art. For example, Nametkin et al. teaches the preparation of silacyclobutane by reduction of 1,1-dichloro-1-silacyclobutane in n-butyl ether at 55–60° C. (Khim. Geterotsikl. Soedin., 1966, 4, 623).

Laane discloses, inter alia, the preparation of silacyclobutane in 60% yield by treatment of lithium aluminum hydride in ethyl ether with 1,1-dicholoro-1-silacyclobutane in n-butyl ether at −5 to +5° C. (J. Am. Chem. Soc. 1967, 89 (5), 1144–1147).

U.S. Pat. No. 4,973,723 to Cawthon et al. discloses the preparation of silacycloalkanes by reduction of halosilacycloalkanes with an alkylaluminum hydride. According to a preferred embodiment of the invention, the halosilacycloalkane is added to the alkylaluminum hydride under temperature and pressure conditions that cause the silacycloalkane to vaporize immediately after it is formed. The silacycloalkane product is vacuum distilled from the resultant mixture immediately upon formation, virtually eliminating the occurrence of further reactions of the silacycloalkane. According to the '723 patent, improved yields of product are achieved by the described process.

Although the aforementioned references describe the preparation of silacycloalkanes by reduction of halosilacycloalkanes, there remains a need for a method of producing silacyclakalanes having high purity in high yield that is scaleable to a commercial manufacturing process.

SUMMARY OF THE INVENTION

The present invention is directed to a method of preparing a silacycloalkane having the formula:

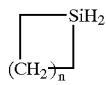

wherein n is 1, 2, or 3, comprising the steps of:

(A) adding a substituted silacycloalkane having the formula:

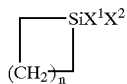

wherein $X^1$ is —F, —Cl, —Br, or —$OR^1$ and $X^2$ is $X^1$ or H, wherein $R^1$ is $C_1$–$C_8$ hydrocarbyl and n is 1, 2, or 3, to a suspension of lithium aluminum hydride in a glycol diether at a temperature not greater than 50° C. to form a mixture, wherein the glycol diether consists essentially of a linear arrangement of oxyalkylene units having formulae independently selected from —$OCH_2CH_2$—, —$OCH_2CH(CH_3)$—, and —$OCH_2CH(CH_2CH_3)$—, and end-groups having the formulae —$R^2$ and —$OR^2$, wherein each $R^2$ is independently $C_1$–$C_8$ alkyl, phenyl, or $C_1$–$C_8$ alkyl-substituted phenyl, provided the glycol diether has a normal boiling point of at least 85° C. and a viscosity not greater than 3000 $mm^2$/s at 25° C.; and (B) distilling the mixture under reduced pressure at a temperature not greater than 50° C. to remove the silacycloalkane.

The method of the present invention produces silacycloalkanes having high purity in high yield. Importantly, the silacycloalkane can be readily and efficiently removed from the reaction mixture by distillation. This separation minimizes the occurrence of unwanted side reactions that can diminish purity and yield. Also, the silacycloalkane product is free of solvent, which can be deleterious in certain applications, particularly in the electronics field. Further, the method can be carried out economically with a stoichiometric amount or only slight excess of lithium aluminum hydride. Still further, the method can be scaled to a commercial manufacturing process.

The silacycloalkanes of the present invention can be used as coatings on solar panels and as precursors for synthesis of various sila drugs. Moreover, the silacycloalkanes can be used to prepare polycarbosilanes, which are useful as ceramic precursors.

These and other features, aspects, and advantages of the present invention will become better understood with reference to the following description and appended claims.

DETAILED DESCRIPTION OF THE INVENTION

According to the present invention, a method of preparing a silacycloalkane having the formula:

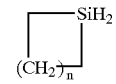

wherein n is 1, 2, or 3, comprising the steps of:

(A) adding a substituted silacycloalkane having the formula:

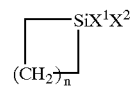

wherein $X^1$ is —F, —Cl, —Br, or —$OR^1$ and $X^2$ is $X^1$ or H, wherein $R^1$ is $C_1$–$C_8$ hydrocarbyl and n is 1, 2, or 3, to a suspension of lithium aluminum hydride in a glycol diether at a temperature not greater than 50° C. to form a mixture, wherein the glycol diether consists essentially of a linear arrangement of oxyalkylene units having formulae independently selected from —$OCH_2CH_2$—, —$OCH_2CH(CH_3)$—, and —$OCH_2CH(CH_2CH_3)$—, and end-groups having the formulae —$R^2$ and —$OR^2$, wherein each $R^2$ is independently $C_1$–$C_8$ alkyl, phenyl, or $C_1$–$C_8$ alkyl-substituted phenyl, provided the glycol diether has a normal boiling point of at least 85° C. and a viscosity not greater than 3000 $mm^2$/s at 25° C.; and (B) distilling the mixture under reduced pressure at a temperature not greater than 50° C. to remove the silacycloalkane.

The substituted silacycloalkane of the present invention has the formula:

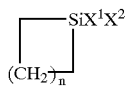

wherein $X^1$ is —F, —Cl, —Br, or —$OR^1$ and $X^2$ is $X^1$ or H, wherein $R^1$ is $C_1$–$C_8$ hydrocarbyl and n is 1, 2, or 3. The hydrocarbyl groups represented by $R^1$ can have from 1 to 8 carbon atoms, alternatively from 1 to 4 carbon atoms. Hydrocarbyl groups having at least three carbon atoms can have a branched or an unranked structure. Examples of hydrocarbyl groups represented by $R^1$ include, but are not limited to, alkyl such as methyl, ethyl, propyl, pentyl, and octyl; cycloalkyl such as cylcohexyl; alkenyl such as vinyl and allyl; and aryl such as phenyl, tolyl, xylyl, benzyl, and 2-phenylethyl. Preferably, $R^1$ is alkyl and more preferably, $R^1$ is methyl, ethyl, or propyl.

Examples of substituted silacycloalkanes include, but are not limited to, 1,1-difluoro-1-silacyclobutane, 1,1-dichloro-1-silacyclobutane, 1,1-dibromo-1-silacyclobutane, 1,1-dimethoxy-1-silacyclobutane, 1,1-difluoro-1-silacyclopentane, 1,1-dichloro-1-silacyclopentane, 1,1-dibromo-1-silacyclopentane, 1,1-dimethoxy-1-silacyclopentane, 1,1-difluoro-1-silacyclohexane, 1,1-dichloro-1-silacyclohexane, 1,1-dibromo-1-silacyclohexane, and 1,1-dimethoxy-1-silacyclohexane.

Furthermore, the substituted silacyclolalkane can be a single substituted silacyclolalkane or a mixture comprising two or more different substituted silacyclolalkanes.

The substituted silacycloalkanes wherein $X^1$ and $X^2$ are —Cl and n is 1 can be prepared using the method of Laane (J. Am. Chem. Soc. 1967, 89 (5), 1144–1147). According to this procedure, (3-chloropropyl)trichlorosilane (0.94 mol) in diethyl ether was added dropwise to a vigorously stirred suspension of magnesium powder (1.7 g-atoms) in ether (500 mL) over a period of 3 hours. The stirred mixture was heated for 72 hours and then allowed to cool to room temperature. The magnesium chloride and excess magnesium metal were removed by filtration and washed several times with ether. The filtrate and washings were combined and distilled to give 1,1-dichloro-1-silacyclobutane (61%) having a boiling point of 113–115° C.

The substituted silacycloalkanes wherein $X^1$ is Cl, $X^2$ is H, and n is 1 can be prepared by substituting (3-chloropropyl)dichlorosilane for (3-chloropropyl)trichlorosilane in the above procedure.

Methods of preparing the substituted silacycloalkanes wherein $X^1$ and $X^2$ are—Cl and n is 2 (1,1-dichloro-1-silacyclobutane) or 3 (1,1-dichloro-1-silacyclopentane) are well known in the art. For example, these compounds can be prepared from the corresponding α,ω-dichloroalkanes or α,ω-dibromoalkanes and silicon tetrachloride by means of the Grignard reaction, as described in *Organosilicon Compounds* (Eaborn, C., Butterworths Scientific Publications: London, 1960, Chapter 13).

The substituted silacycloalkanes wherein $X^1$ is —Cl, $X^2$ is H, and n is 2 or 3 can be prepared by substituting trichlorosilane for silicon tetrachloride in the above procedure.

The substituted silacycloalkanes wherein $X^1$ and $X^2$ are —Br and n is 1, 2, or 3 can be prepared by treating the corresponding 1,1-dichloro-1-silacycloalkanes with molecular bromine. The exchange reactions between organosilicon halides and molecular halogens are well known in the art, as exemplified in *Organosilicon Compounds* (Eaborn, C., Butterworths Scientific Publications: London, 1960; pp 187–188).

The substituted silacycloalkanes wherein $X^1$ is —Br, $X^2$ is H, and n is 1, 2, or 3 can be prepared similarly by treating the corresponding 1-chloro-1-silacycloalkanes with molecular bromine.

The substituted silacycloalkanes wherein $X^1$ and $X^2$ are —F and n is 1, 2, or 3 can be prepared by treating the corresponding 1,1-dichloro- or 1,1-dibromo-1-silacycloalkanes with various metal fluorides. Examples of suitable metal fluorides include, but are not limited to, $ZnF_2$, NaF, CsF, $SbF_5$, and $CoF_2$. The conversion of organochlorosilanes and organobromosilanes to the corresponding organofluorosilanes by treatment of the former with metal fluorides, ammonium fluoride, or sodium borofluoride in acetone, is well known in the art, as exemplified in *Organosilicon Compounds* (Eaborn, C., Butterworths Scientific Publications: London, 1960, pp 173–175).

The substituted silacycloalkanes wherein $X^1$ is —F, $X^2$ is H, and n is 1, 2, or 3 can be similarly prepared by treating the corresponding 1-chloro- or 1-bromo-1-silacycloalkanes with metal fluorides.

The substituted silacycloalkanes wherein $X^1$ and $X^2$ are $OR^1$ and n is 1, 2, or 3, where $R^1$ is as defined and exemplified above, can be prepared by contacting the corresponding 1,1-difluoro-, 1,1-dichloro-, or 1,1-dibromo-1-silacycloalkanes with at least two equivalents, based on the number of moles of silacycloalkane, of an alcohol or phenol. The reaction of the halosilacycloalkane and alcohol or phenol can be carried out in the presence of a base, such as pyridine or a tertiary amine, which combines with the liberated HCl. Preferably, the alcohol or phenol is substantially free of water. The reaction of the alcohol or phenol with the halosilacycloalkane can be carried out in an inert solvent such as ether or toluene. The reaction is frequently carried out using excess alcohol or phenol as the solvent.

The substituted silacycloalkanes wherein $X^1$ is —$OR^1$, $X^2$ is H, and n is 1, 2, or 3 can be prepared similarly by treating the corresponding 1-chloro- or 1-bromo-1-silacycloalkanes with at least one equivalent, based on the number of moles of silacycloalkane, of an alcohol or phenol.

The lithium aluminum hydride is commercially available in solid form, e.g., a powder or pellets. Solutions of lithium aluminum hydride in various solvents are also commercially available. However, low boiling solvents such as diethyl ether, diglyme, ethylene glycol dimethyl ether, tetrahydrofuran, and toluene can distill with the silacycloalkane and contaminate the product. Such contamination can cause problems in certain applications, particularly in the electronics field, that require high purity. The lithium aluminum hydride is combined with the glycol diether to form a suspension.

The glycol diether of the present method consists essentially of a linear arrangement of oxyalkylene units having formulae independently selected from —$OCH_2CH_2$—, —$OCH_2CH(CH_3)$—, and —$OCH_2CH(CH_2CH_3)$—, and end-groups having the formulae —$R^2$ and —$OR^2$, wherein each $R^2$ is independently $C_1$–$C_8$ alkyl, phenyl, or $C_1$–$C_8$ alkyl-substituted phenyl. Examples of alkyl groups represented by $R^2$ include, but are not limited to, methyl, ethyl, propyl, pentyl, hexyl, heptyl, and octyl. Examples of alkyl-substituted phenyl groups represented by $R^2$ include, but are not limited to, tolyl, xylyl, benzyl, and 2-phenylethyl.

The glycol diether can be a dimer, trimer, oligomer, or polymer. The oxyalkylene units in the glycol diether can be connected head-to-tail, head-to-head, or tail-to-tail. The glycol diether can be a homopolymer or a copolymer, such as a random, alternating, periodic, or block copolymer. When the glycol diether contains at least two types of oxyalkylene units, the units can be sequentially arranged in any manner. Furthermore, the glycol diether can be a single glycol diether or a mixture comprising two or more different glycol diethers.

The glycol diether has a normal boiling point of at least 85° C., alternatively at least 100° C., alternatively at least 200° C. When the normal boiling point of the glycol diether is less than 85° C., the diether can distill with the silacycloalkane and contaminate the product.

The glycol diether is a liquid having a viscosity at 25° C. not greater than 3000 mm$^2$/s, alternatively not greater than 2000 mm$^2$/s, alternatively not greater than 1000 mm$^2$/s. When the viscosity of the glycol diether is greater than 3000 mm$^2$/s, the reaction mixture is very viscous, resulting in less efficient admixing of the lithium aluminum hydride and substituted silacycloalkane. Nonuniform distribution of the co-reactants in the reaction mixture can result in formation of undesirable byproducts, diminishing the yield and purity of the silacycloalkane. Also, a highly viscous reaction mixture can hinder removal of the silacycloalkane by distillation.

Examples of glycol diethers include, but are not limited to, poly(ethylene glycol) dimethyl ether, diethylene glycol dibutyl ether, diethylene glycol diethyl ether, ethylene glycol diethyl ether, tetraethylene glycol dimethyl ether, triethylene glycol dimethyl ether, diethylene glycol dimethyl ether, and ethylene glycol dimethyl ether.

Methods of preparing glycol diethers are well known in the art; many of these compounds are commercially available.

The method of the present invention can be carried out in any standard reactor suitable for contacting lithium aluminum hydride with an organohalosilane. Suitable reactors include glass and Teflon-lined glass reactors. Preferably, the reactor is equipped with a means of agitation, such as stirring.

In the method of the present invention, the substituted silacycloalkane is necessarily added to the suspension of lithium aluminum hydride. Reverse addition, i.e., addition of lithium aluminum to the substituted silacycloalkane, produces a complex mixture of products that are not easily separated by distillation. Consequently, both the yield and purity of the silacycloalkane are diminished compared with the method of the present invention.

The rate of addition of the substituted silacycloalkane to the suspension of lithium aluminum hydride in the glycol diether is sufficiently slow to minimize distillation of the substituted silacylcoalkane from the reaction mixture in step (B) of the present method. Typically, the rate of addition is such that the distillate contains less than 20% (GC area %), alternatively less than 10% (GC area %) of the substituted silacycloalkane, as determined using the gas chromatography method in the Examples below. The rate of addition depends on factors such as reactor size, stirring efficiency, and temperature control. For example, the rate of addition can be from 1 to 4 mL/min., alternatively from 1 to 3 mL/min., alternatively from 2 to 3 mL/min, for a 100 mL reaction vessel equipped with an efficient means of stirring. Also, the rate of addition can be from 10 to 40 mL/min., alternatively from 10 to 30 mL/min., alternatively from 20 to 30 mL/min, for a 1 L reaction vessel equipped with an efficient means of stirring. When the rate of addition is too slow, the reaction time is unnecessarily prolonged. When the rate of addition is too fast, byproducts are formed, which reduce the yield and purity of the silacycloalkane. The optimum rate of addition can be easily determined by routine experimentation using the methods described in the Examples below.

The substituted silacycloalkane can be added to the suspension of lithium aluminum hydride in the glycol diether at a temperature not greater than 50° C., alternatively not greater than 30° C., alternatively not greater than 0° C. At a temperature greater than 50° C., the silacycloalkane may decompose. The minimum temperature of the reaction mixture is determined by the freezing points of the substituted silacycloalkane, glycol diether, and silacycloalkane product. The substituted silacycloalkane is added to the suspension of lithium aluminum hydride in the glycol diether at a temperature greater than the freezing point of any of the substituted silacycloalkane, glycol diether, and silacycloalkane product The substituted silacycloalkane can be added directly to the suspension of lithium aluminum hydride or diluted in a glycol diether and added to the mixture.

The mole ratio of lithium aluminum hydride to the substituted silacycloalkane can be from 0.5 to 3, alternatively from 0.5 to 1.2, alternatively from 0.5 to 0.7. When the mole ratio of lithium aluminum hydride to substituted silacycloalkane is less than 0.5, significant amount of the unsubstituted silacycloalkane fails to react. When the mole ratio is greater than 3, the cost of the process is increased unnecessarily.

The mole ratio of the glycol diether to the substituted silacycloalkane can be from 0.3 to 5, alternatively from 1 to 3, alternatively 1.5 to 2.5. When the mole ratio of glycol diether to substituted silacycloalkane is less than 0.3, the viscosity of the reaction mixture may be too high for efficient mixing. When the mole ratio is greater than 5, the cost of the process is increased unnecessarily.

The reaction mixture is distilled under reduced pressure at a temperature not greater than 50° C. As used herein, the term "reduced pressure," means a pressure less than atmospheric pressure sufficient to volatilize the silacycloalkane and remove it from the reaction mixture. The particular pressure depends on the distillation temperature. For example, the pressure can be from 0.1 to 20 kPa at a temperature of from –20 to +25° C., alternatively from 13 to 20 kPa at a temperature of from 5 to 25° C. As the distillation temperature increases in the above ranges, the pressure required for volatilization of the silacycloalkane decreases. The optimum pressure at a particular temperature can be readily determined by routine experimentation.

Steps (A) and (B) of the present invention can be carried out in sequential order or simultaneously. For example, the substituted silacycloalkane can be added to the suspension of lithium aluminum hydride in the glycol diether followed by distillation of the reaction mixture under reduced pressure to remove the silacycloalkane. In this embodiment of the present invention, the addition of the substituted silacycloalkane, step (A), is preferably carried out in the substantial absence of atmospheric oxygen or moisture. This can be accomplished by purging the reactor with a dry inert gas, such as argon or nitrogen prior to introduction of the reactants and thereafter maintaining a blanket of the gas in the reactor.

Alternatively, the silacycloalkane can be added to the suspension of lithium aluminum hydride under reduced pressure with concomitant distillation of the reaction mixture to remove the silacycloalkane as it is formed, thus minimizing the occurrence of unwanted side reactions that can diminish purity and yield.

If desired, the silacycloalkane obtained by the method of the present invention can be further purified by at least one more distillation at a temperature less than 50° C. under reduced pressure.

The method of the present invention produces silacycloalkanes having high purity in high yield. Importantly, the silacycloalkane can be readily and efficiently removed from the reaction mixture by distillation. This separation minimizes the occurrence of unwanted side reactions that can diminish purity and yield. Also, the silacycloalkane product is free of solvent, which can be deleterious in certain applications, particularly in the electronics field. Further, the method can be carried out economically with a stoichiometric amount or only slight excess of lithium aluminum hydride. Still further, the method can be scaled to a commercial manufacturing process.

The silacycloalkanes of the present invention can be used as coatings on solar panels and as precursors for synthesis of various sila drugs. Moreover, the silacycloalkanes can be used to prepare polycarbosilanes, which are useful as ceramic precursors.

EXAMPLES

The following examples are presented to further illustrate the method of the present invention, but are not to be considered as limiting the invention, which is delineated in the appended claims.

Analysis of Reaction Products

Gas chromatography was performed using a Hewlett Packard 5890 gas chromatograph equipped with a 20 in.×⅛ in. HP 80 mesh column (SE 30 on Chromosorb W) operated isothermally at 160° C., an FID detector, and a Hewlett Packard 3392A recording integrator. Mass spectrometry was performed using the above gas chromatograph with an HP 5970 Series Selective detector.

Reagents

The following chemical substances were used in the Examples:

Lithium aluminum hydride, powder (95+%) is available from Aldrich (Milwaukee, Wis.).

Diethylene glycol dibutyl ether (99+%) is available from Aldrich (Milwaukee, Wis.).

(3-Chloropropyl)trichlorosilane (97%) is available from Lancaster Synthesis Inc. (Windham, N.H.).

Example 1

Diethyl ether (1.5 L), tetrahydrofuran (1.5 L), and magnesium (120 g) were combined under argon in a 5-L round bottom flask equipped with an overhead stirrer, reflux condenser, and addition funnel. (3-Chloropropyl) trichlorosilane (600 g, 3.26 mol) was added to the stirred solution at a rate sufficient to maintain gentle reflux during a period of about 4 h. After the addition was complete, the resulting slurry was heated to reflux for 3 h and then stirred at room temperature overnight. The slurry was filtered to remove the salts, which were washed with pentane. The washing and filtrate were combined and distilled at atmospheric pressure to remove the solvents. The residue was then fractionally distilled in vacuo through a Vigreaux column (3 ft, 0.91 m) to give 1,1-dichloro-1-silacyclobutane (250 g, 1.77 mol, 55% yield, >98% purity by GC) as a colorless liquid having a boiling point of about 55° C. at 115 mmHg (15.3 kPa).

Example 2

Lithium aluminum hydride, powder, (100 g, 2.63 mol) and diethylene glycol dibutyl ether (1012 g, 4.64 mol) were combined under argon in a 2-L three-neck flask equipped with a mechanical stirrer, addition funnel, and a three-way adapter connected to a thermometer, vacuum adapter, and multi-flask receiver assembly. The temperature of the mixture was adjusted to 20° C. and then the pressure was reduced to about 1 mmHg (133 Pa). While maintaining the temperature at 20° C., 1,1-Dichloro-1-silacyclobutane (295 g, 2.09 mol) was added drop wise to the mixture over a period of 3 h, during which time the product was continuously removed from the mixture by distillation. After the addition was complete, an empty receiving flask was rotated into position, 1,1-dichloro-1-silacyclobutane (95 g, 0.67 mol) was again added drop wise to the reaction mixture, and the product was continuously removed by distillation.

The product (142.8 g) from the first addition of 1,1-dichloro-1-silacacylcobutane consisted of silacyclobutane (79.6 GC area %) and 1,1-dichloro-1-silacyclobutane (18.0 GC area %). The product (42.6 g) from the second addition of 1,1-dichloro-1-silacacylcobutane consisted of silacyclobutane (75.8 GC area %) and 1,1-dichloro-1-silacyclobutane (21.0 GC area %).

Example 3

Lithium aluminum hydride, powder, (100 g, 2.63 mol) and diethylene glycol dibutyl ether (783 g, 3.59 mol) were combined under argon in a 2-L three-neck flask equipped with a mechanical stirrer, addition funnel, and a three-way adapter connected to a thermometer, vacuum adapter, and multi-flask receiver assembly. The temperature of the mixture was adjusted to 10° C. and then the pressure was reduced to about 1 mmHg (133 Pa). While maintaining the temperature at 10° C., 1,1-Dichloro-1-silacyclobutane (297 g, 2.11 mol) was added drop wise to the mixture over a period of 1.5 h, during which time the product was continuously removed from the mixture by distillation. After the addition was complete, an empty receiving flask was rotated into position, 1,1-dichloro-1-silacyclobutane (93.3 g, 0.661 mol) was again added drop wise to the reaction mixture, and the product was continuously removed from the mixture by distillation.

The product (106.7 g) from the first addition of 1,1-dichloro-1-silacacylcobutane consisted of silacyclobutane (94.6 GC area %) and 1,1-dichloro-1-silacyclobutane (3.9 GC area %). The product (35.4 g) from the second addition of 1,1-dichloro-1-silacacylcobutane consisted of silacyclobutane (96.1 GC area %) and 1,1-dichloro-1-silacyclobutane (2.64 GC area %).

Example 4

Lithium aluminum hydride, powder, (100 g, 2.63 mol) and diethylene glycol dibutyl ether (984 g, 4.51 mol) were combined under argon in a 2L three-neck flask equipped with a mechanical stirrer, addition funnel, and a three-way adapter connected to a thermometer, vacuum adapter, and multi-flask receiver assembly. The temperature of the mixture was adjusted to 0° C. and then the pressure was reduced to about 1 mmHg (133 Pa). While maintaining the temperature at 0° C., 1,1-Dichloro-1-silacyclobutane (298 g, 2.11 mol) was added drop wise to the mixture over a period of 2.5 h, during which time the product was continuously removed by distillation. After the addition was complete, an empty receiving flask was rotated into position, 1,1-dichloro-1-silacyclobutane (91 g, 0.65 mol) was again added drop wise to the reaction mixture, and the product was continuously removed by distillation. In a similar manner, a third portion of 1,1-dichloro-1-silacyclobutane (120 g, 0.851 mol) and a fourth portion of 1,1-dichloro-1-silacyclobutane (65 g, 0.46 mol) were sequentially added to the reaction mixture. The product formed during each addition was continuously removed by distillation and collected in a fresh receiving flask.

The product (146.3 g) from the first addition of 1,1-dichloro-1-silacacylcobutane consisted of silacyclobutane (97.4 GC area %) and 1,1-dichloro-1-silacyclobutane (1.1 GC area %). The product (43.4 g) from the second addition of 1,1-dichloro-1-silacacylcobutane consisted of silacyclobutane (92.3 GC area %) and 1,1-dichloro-1-silacyclobutane (7.6 GC area %). The product from the third addition (59.1 g) and the product from the fourth addition (33.1 g) of 1,1-dichloro-1-silacacylcobutane were combined to afford a crude product consisting of silacyclobutane (93.3 GC area %) and 1,1-dichloro-1-silacyclobutane (6.6 GC area %). All the products were combined and fractionally distilled in vacuo to give silacyclobutane (99.6 GC area %) as a colorless liquid having a boiling point of about 7° C. at 170 mmHg (22.7 kPa).

That which is claimed is:

1. A method of preparing a silacycloalkane having the formula:

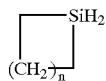

wherein n is 1, 2, or 3, comprising the steps of:
(A) adding a substituted silacycloalkane having the formula:

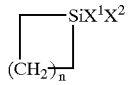

wherein $X^1$ is —F, —Cl, —Br, or —$OR^1$ and $X^2$ is $X^1$ or H, wherein $R^1$ is $C_1$–$C_8$ hydrocarbyl and n is 1, 2, or 3, to a suspension of lithium aluminum hydride in a glycol diether at a temperature not greater than 50° C. to form a mixture, wherein the glycol diether consists essentially of a linear arrangement of oxyalkylene units having formulae independently selected from —$OCH_2CH_2$—, —$OCH_2CH(CH_3)$—, and —$OCH_2CH(CH_2CH_3)$—, and end-groups having the formulae —$R^2$ and —$OR^2$, wherein each $R^2$ is independently $C_1$–$C_8$ alkyl, phenyl, or $C_1$–$C_8$ alkyl-substituted phenyl, provided the glycol diether has a normal boiling point of at least 85° C. and a viscosity not greater than 3000 mm$^2$/s at 25° C.; and
(B) distilling the mixture under reduced pressure at a temperature not greater than 50° C. to remove the silacycloalkane.

2. The method according to claim 1, wherein the hydrocarbyl group represented by $R^1$ has from 1 to 4 carbon atoms.

3. The method according to claim 1, wherein $X^1$ and $X^2$ are —Cl.

4. The method according to claim 3, wherein n is 1.

5. The method according to claim 1, wherein the glycol diether is a dimer, trimer, or oligomer.

6. The method according to claim 5, wherein the glycol diether is diethylene glycol dibutyl ether.

7. The method according to claim 1, wherein the glycol diether has a normal boiling point of at least 100° C.

8. The method according to claim 7, wherein the glycol diether has a normal boiling point of at least 200° C.

9. The method according to claim 1, wherein the glycol diether has a viscosity at 25° C. not greater than 3000 mm$^2$/s.

10. The method according to claim 9, wherein the glycol diether has a viscosity at 25° C. not greater than 2000 mm$^2$/s.

11. The method according to claim 1, the rate of addition of the substituted silacycloalkane to the suspension of lithium aluminum hydride in the glycol diether is sufficiently slow to minimize distillation of the substituted silacylcoalkane from the reaction mixture.

12. The method according to claim 11, wherein the rate of addition is such that the distillate contains less than 20% (GC area %) of the substituted silacycloalkane.

13. The method according to claim 11, wherein the rate of addition is such that the distillate contains less than 10% (GC area %) of the substituted silacycloalkane.

14. The method according to claim 1, wherein the mole ratio of lithium aluminum hydride to the substituted silacycloalkane is from 0.5 to 3.

15. The method according to claim 14, wherein the mole ratio of lithium aluminum hydride to the substituted silacycloalkane is from 0.5 to 1.2.

16. The method according to claim 1, wherein the mole ratio of the glycol diether to the substituted silacycloalkane is from 0.3 to 5.

17. The method according to claim 16, wherein the mole ratio of the glycol diether to the substituted silacycloalkane is form 1 to 3.

18. The method according to claim 1, wherein the step (B) is carried out at a pressure of from 0.1 to 20 kPa and a temperature of from –20 to +25° C.

19. The method according to claim 1, wherein step (A) and step (B) are carried out in sequential order.

20. The method according to claim 1, wherein step (A) and step (B) are carried out simultaneously.

* * * * *